(12) United States Patent
Irgum et al.

(10) Patent No.: US 6,884,345 B1
(45) Date of Patent: Apr. 26, 2005

(54) CHROMATOGRAPHY METHOD AND A COLUMN MATERIAL USEFUL IN SAID METHOD

(76) Inventors: Knut Irgum, Tålsmark 8, Bullsmark (SE), SE-912 92; Camilla Viklund, Rödhakevägen 58A, Umeå (SE), SE-906 51

(*) Notice: Subject to any disclaimer, the term of this patent is extended or adjusted under 35 U.S.C. 154(b) by 0 days.

(21) Appl. No.: 09/831,162
(22) PCT Filed: Nov. 9, 1999
(86) PCT No.: PCT/SE99/02032
§ 371 (c)(1),
(2), (4) Date: May 7, 2001
(87) PCT Pub. No.: WO00/27496
PCT Pub. Date: May 18, 2000

(30) Foreign Application Priority Data

Nov. 9, 1998 (SE) .............................................. 9803838

(51) Int. Cl.[7] ............................................ B01D 15/08
(52) U.S. Cl. ............................... 210/198.2; 210/502.1; 210/635; 210/656; 502/402; 502/404
(58) Field of Search ................................ 210/635, 656, 210/659, 198.2, 502.1; 502/402, 404

(56) References Cited

U.S. PATENT DOCUMENTS

| | | | | |
|---|---|---|---|---|
| 4,577,013 A | * | 3/1986 | Merz | 210/656 |
| 5,589,069 A | | 12/1996 | Wenzhi | 210/635 |
| 6,039,876 A | * | 3/2000 | Yang | 210/635 |
| 6,074,979 A | * | 6/2000 | Hagemeyer | 502/159 |
| 6,238,565 B1 | * | 5/2001 | Hatch | 210/635 |
| 6,391,818 B1 | * | 5/2002 | Bonsel | 502/159 |

FOREIGN PATENT DOCUMENTS

WO    WO 98/49279    11/1998    .............. 210/635

OTHER PUBLICATIONS

Snyder, Introduction to Modern Liquid Chromatography, John Wiley and Sons, 1979, pp. 493–499.*
Yu (Journal of Chromatographic Science, vol. 24, May 1986, pp. 177–182.*
Yu (Journal of Chromatographic Science, vol. 27 Apr. 1989, pp. 176–185.*
Kurganov (Journal of Chromatography, 548 (1991) pp. 207–214.*
Viklund (Biotechnol. 1997, 13, 597–600).*
Hatch (Industrial and Engineering Chemistry, vol. 49 No. 11 Nov. 1957, pp. 1812–1819.*
Grote (Reactive & Functional Polymers, 35 (1997) pp. 179–196.*

* cited by examiner

Primary Examiner—Ernest G. Therkorn
(74) Attorney, Agent, or Firm—Young & Thompson

(57) ABSTRACT

A novel sorbent suitable for use as a stationary phase in a chromatography column, the core of which consists of an organic polymer of synthetic or natural origin. Further, the carrier exhibits a plurality of covalently bonded non-aromatic zwitterionic groups on its surface. Additionally, the invention also relates to a method for purifying a particular biological macromolecule, such as a protein or a nucleic acid, by zwitterionic ion exchange chromatography as well as an ion exchange column suitable for use in the zwitterionic ion exchange chromatography.

20 Claims, 9 Drawing Sheets

A)

SC = Sorbent carrier

B)

SC = Sorbent carrier

A)

SC = Sorbent carrier

B)

SC = Sorbent carrier

Retention time, min

CHROMATOGRAPHY METHOD AND A COLUMN MATERIAL USEFUL IN SAID METHOD

REFERENCE TO RELATED APPLICATIONS

This application is a 371 of PCT/SE99/02032 Nov. 9, 1999.

TECHNICAL FIELD

The present invention relates to a novel ion-exchange chromatography method suitable for separating biological macromolecules. The method is based upon using sorbents on which zwitterionic functional groups have been bound. The invention also relates to a novel sorbent on which zwitterionic pendant groups have been covalently bound.

TECHNICAL BACKGROUND

Ion-exchange chromatography (IEC) is the most widely used chromatographic tool in protein purification schemes, and is performed either as a high- or low pressure technique. Ion-exchange sorbents are usually based on inorganic silica beads or polymeric particles, which are provided with surface cationic or anionic groups capable of interacting electrostatically with ionic species of opposite charge. The retention of a protein will thus depend on the charge status of the protein, the amount of interaction sites available on the sorbent, and on the strength of the individual interactions. Displacement of the analyte is normally achieved by competitively increasing the mobile-phase ionic strength, and relatively high salt concentrations are often required in order to elute even moderately retained proteins [Deutscher, M. P. (Ed.), Guide to Protein Purification (Meth. Enzymol., Vol. 182), Academic Press, 1990]. Even if many proteins can withstand high salt concentrations without severe denaturation, there are usually other practical limits to the ionic strength of the eluent, such as "salting out", or the desire to produce a separated sample in a relatively low saline buffer to avoid extensive dialysis of the solute after the separation. An ideal ion-exchange sorbent should also be free from non-specific interaction sites, possess an internal porosity that allows even large proteins to enter, and have a permeability and a mechanical rigidity sufficient for operation at high flow rates (Müller, W., *J Chromatogr.,* 1990, 510, 133–140).

Accordingly, there is a need for an improved ion-exchange chromatography method which does not require elution using high salt concentrations, and which fulfills as many of the above mentioned criteria regarding ideal ion-exchange sorbents as possible.

Because of tie significance of bioseparations both in industry and in research, there is a never ending search for novel stationary phases that can fulfill up-coming requirements. In particular, there is an interest in new separation modes, which can provide selectivities that are orthogonal to existing techniques. In 1992, Svec and Fréchet pioneered a novel kind of separation media consisting of a rigid macroporous monoliths polymerized in-situ within the confines of a chromatographic column (Svec, F.; Fréchet, J. M. J. *Anal. Chem.* 1992, 64, 830–832). The porous properties of these monoliths can be easily controlled during their synthesis (Viklund, C.; Svec, F.; Fréchet J. M. J.; Irgum, K. *Chem. Mater.* 1996, 8, 744–750; Viklund, C.; Ponten, E.; Glad, B.; Irgum, K. Svec, F.; Hörstedt, P. *Chem. Mater.* 1997, 9, 463–471), which makes it possible to design materials suitable for a particular bioseparation application. For example, poly(glycidyl methacrylate-co-ethylene dimethacrylate) monoliths modified to contain diethylamine functional groups have been used in anion exchange mode for the separation of proteins (Svec, F.; Fréchet, J. M. J., *Anal. Chem.* 1992, 64, 830–832; Svec, F.; Fréchet, J. M. J., *J. Chromatogr. A.* 1995b, 702, 89–95). Poly(styrene-co-divinylbenzene) monolithic columns have been successfully used for the fast separation of proteins in the reversed phase mode (Wang, Q. C.; Svec, F.; Fréchet, J. M. J. *Anal. Chem.* 1993, 65, 2243–2248), and it has recently been shown that polyacrylamide based monoliths can be used for the rapid separation of proteins in the hydrodynamic interaction mode when butyl methacrylate is included in tie polymerization mold (Xie, S.; Svec, F.; Fréchet, J. M. J., *J. Chromatogr. A.,* 1997, 775, 65–72). It has also recently been demonstrated that a porous monolithic column grafted with 2-acrylamido-2-methyl-1-propane sulfonic acid can be used for fast cation exchange chromatography of basic proteins (Viklund, C.; Svec, F.; Fréchet, J. M. J.; Irgum, K., *Biotechnol. Progr.,* 1997, 13, 597–600).

Experiments with multiple mode ion exchange chromatographic separations have been done with tandem connection of anion exchange and cation exchange columns in series (E l Rassi Z.; Horwath, C. *J. Chromatogr.,* 1986, 359, 255), and with columns containing mixes of both anion and cation exchange sorbents (Maa, Y. F.; Antia, F.; E l Raasi, Z.; Horwath, C. *J. Chromatogr.,* 1988, 452, 331). Protein separations on mixed cation and anion exchange media have also been carried out on stacks of alternating cation and anion exchange membranes, spaced by neutral membranes (Freitag, R.; Splitt, H; Reif, O.-W., J. Chromatogr., 1996, 728, 129–37).

Chromatographic techniques utilizing zwitterionic moieties in the stationary phase or in the eluent have gained interest since 1981, when Knox and Jurand introduced a technique where quadropolar ion-pairs could be formed when 11-amino undecanoic acid was added to the eluting solution as a "zwitterion-pair agent" (Knox, J. H.; Jurand, J. a) *J. Chromatogr.* 1981, 203, 85–92; b) *J. Chromatogr.* 1981, 218, 341–354; *J. Chromatogr.* 1981, 218, 355–363; *J. Chromatogr.* 1982, 234, 222–224). This concept was seen to improve the retention of various nucleotides and oligopeptides comprising up to three amino acids in reversed phase chromatography.

Kurganov and co-workers (Kurganov, A. A.; Davankov, V. A.; Unger, K. K. *J. Chromatogr.* 1991, 548, 207–214) were able to separate acidic and/or basic proteins using a stationary phase which contained both sulfonic acid and quaternary ammonium groups. This mixed mode sorbent, incorrectly termed as being a zwitterionic sorbent in said paper, was prepared by introduction of sulfonic acid and quaternary ammonium groups by sequential chloromethylation, sulfonation and trimethylamination of a styrene layer superficially polymerized onto silica. This will result in ion exchange groups of different charge residing on separate phenyl moieties in the superficial layer, and on p. 212 of said paper, two important aspects are disclosed, that clearly distinguish this mixed mode sorbent from a true zwitterionic sorbent, as disclosed in this document, namely: a) "The result reveal that the ion exchanger contains cationic groups in excess of anion exchange groups" and b) "The peak of lysozyme (last eluting peak) is relatively broad, even at the high flow rate used for elution. It seems that this broadening is due to the mixed-mode interactions between lysozyme and the exchanger.".

Another example of a mixed mode sorbent is by Nomura and co-workers (Nomura, A.; Yamada, J.; Tsunoda, K. *Anal.*

Chem. 1988, 60, 2509–2512), who reported the preparation of a silica-based HPLC stationary phase onto which amino-containing compounds and carboxy-containing groups, respectively, are independently immobilised. The suitability of this, in reality amphoteric, sorbent for protein separation was also explored. However, no satisfactory results were obtained as some proteins were very strongly adsorbed, and accordingly they were very difficult to elute.

Among the first polymeric carriers intentionally designed to contain a mixture of anion and cation exchange resins were so-called "snake cage resins", made by polymerizing an acrylic acid "snake" that had been carefully equilibrated with an anion exchange resin (the "cage") in order to obtain a stoichiometry between the resulting cation and anion exchange sites (Hatch, M. J.; Dillon, A.; Smith, H. B. *Ind. Eng. Chem.*, 1957, 49, 1812). The resulting sorbents were used as "ion retardation resins", e.g., for desalting of sugar syrup. Although conceptually a 1:1 stoichiometry should be obtained, there were problems manufacturing these sorbents without net ion exchange properties, which are believed to be due to uneven "patchy" distribution of the ion exchange groups in the sorbent (Small, H. *Ion Chromatography*, Plenum Press: New York, 1989, pp. 133–134). Yu et al. (a) Yu, L. W.; Hartwick, R. A. *J. Chromatogr. Sci.* 1989, 27, 176–185; b) Yu, L. W.; Floyd, T. R; Hartwich, R. A. *J. Chromatogr. Sci.* 1986, 24, 177–182) described the preparation of a chemically bonded zwitterionic silica sorbent, and also showed its potential for the separation of nucleotides. No satisfactory results regarding separation of proteins have been reported for this material. In a large number of papers, Hu and co-workers (a) Hu, W.; Takeuchi, T.; Haraguchi, H. *Anal. Chem.* 1993, 65, 2204–2208; b) Hu, W.; Tao, H.; Haraguchi, H. 1994, 66, 2514–2520) have conducted studies where commercial octadecyl silica columns have been dynamically coated with commercial zwitterionic surfactant reagents. According to their strategy, the zwitterionic surfactant reagents are non-covalently adsorbed to the columns. Using this strategy, simultaneous separation of inorganic cations and anions could be achieved using pure water as the mobile phase. One important reason for using water as the mobile phase is to minimise washing away zwitterionic surfactant during separations. The surfactant has in some cases been included in the eluting solution in order to replace detergents that are continuously washed away from the ODS-column during separations. Hu claims to have separated purified alpha-amylase from saliva on such detergent-modified hydrophobic silica. However, it is important to note that this enzyme passed through the column without retardation as in gel filtration for desalting purposes, and they interpreted their results as being solely due to a size exclusion effect (U.S. Pat. No. 5,589,069; Col. 12, Line 29–31). No other protein was assayed simultaneously, which means that it has not been clarified if the detergent-based dynamic modification method of Hu has the ability of separating different proteins. Finally, it is also important to point out that it is unacceptable in the pharmaceutical industry to use a separation column where part of the column material is leaking out together with compounds that are to be used in pharmaceutical preparations. Polyzwitterions synthesised from zwitterionic monomers have mostly been studied in the field of polymer chemistry because of their fascinating rheological behaviour (Soto, M.; Galin, V. M. *Polymer*, 1984, 25, 254; Schulz, D. N.; Peiffer, D. G.; Agarwal, P. K.; Larabee, J.; Kaladas, J. J.; Soni, L.; Handwerker, B.; Garner, R. T. *Polymer*, 1986, 27, 1734–1742; Huglin, M. B.; Rego, J. M. *Macromolecules*, 1991, 24, 2556–2563) rather than being utilized for chromatographic separation purposes. The most intensively studied class of zwitterion polymers is prepared from monomers with sulfobetaine functionalities, in which the cationic functionality (a quaternary ammonium group) and the anionic functionality (a sulfonate group) are incorporated in close proximity in pendant side chains on the main polymer chain, and it is thus possible to obtain a polymer with zero net charge. It is assumed that the solution behavior of non-crosslinked polyzwitterions is a result of Coulomb interactions between charged groups, and the electrolyte concentration in the surrounding aqueous media will thus have a great influence on the polymer solubility (Soto, M.; Galin, V. M. *Polymer*, 1984, 25, 254; Schulz, D. N.; Peiffer, D. G.; Agarwal, P. K.; Larabee, J.; Kaladas, J. J.; Soni, L.; Handwerker, B.; Garner, R. T. *Polymer*, 1986, 27, 1734–1742; Huglin, M. B.; Rego, J. M. *Macromolecules*, 1991, 24, 2556–2563). In the field of zwitterionic polymeric sorbents, Grote and Schumacher (Grote, M.; Schumacher, U. *React. Funct. Polym.*, 1997, 35, 179–196) have prepared a series of sorbents containing tetrazolinium anion exchange groups, one of which also contained a benzenesulfonic acid group attached to the tetrazolinium ring, thus comprising a zwitterionic group. This sorbent was used for recovery of precious metals.

SUMMARY OF THE INVENTION

It has now turned out that by using porous sorbent carriers as stationary phase in a chromatographic separation process, wherein the core of said sorbent carriers consists of an organic resin, and wherein said sorbent carriers are comprised of a polymer or copolymer comprising monomer units containing zwitterionic non-aromatic aromatic groups throughout its structure or comprising zwitterionic non-aromatic groups covalently grafted or bonded on its surface as pendant moieties, it is possible to carry out ion exchange chromatography separations of biological macromolecules such as proteins using very mild and non-denaturating conditions.

BRIEF DESCRIPTION OF THE DRAWINGS

myoglobin, α-chymotrypsinogen A, cytochrome C and lysozyme on column according to the invention.

DEFINITIONS

Figure 1:
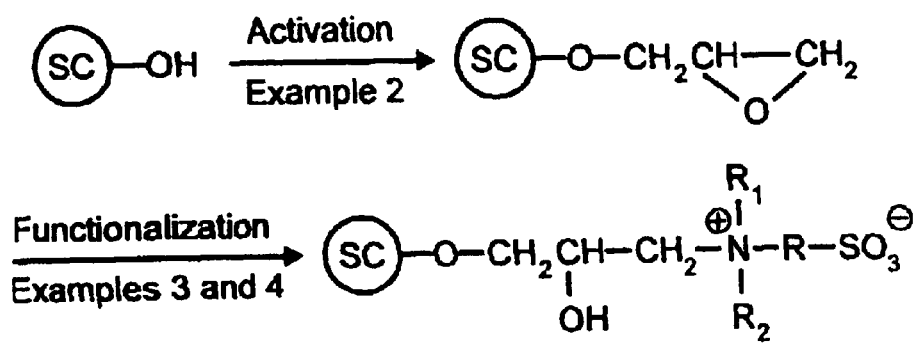
FIG. 1 shows schematic representations of A) the activation and functionalization reactions carried out according to Examples 2–4 below and B) a zwitterionic functionalization reaction based on chemical reactions known to those skilled in the field, that will result in zwitterionic sorbents useful for practising the invention.
Figure 1:
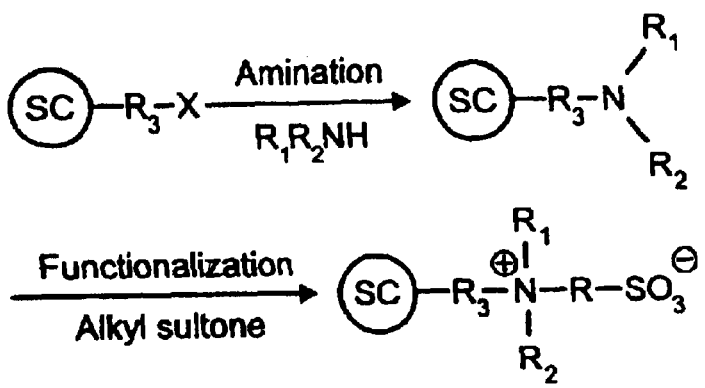

As disclosed herein, the term "sorbent" relates to a material with selective sorption properties that can be used as a stationary phase in chromatographic separations.

As disclosed herein, the composite term "sorbent carrier" relates to a material with mechanical and flow dynamic properties that make it suitable for use as supporting structure for a stationary phase in chromatographic separations.

As used herein, the term "porous monolithic sorbent carrier" relates to a structure comprising pore channels suitably sized for use as sorbent carrier in ion exchange chromatography and high performance liquid chromatography (HPLC) processes.

As disclosed herein, the term "organic resin" refers to an organic polymer or copolymer of synthetic or natural origin comprising mono- or oligovinyl monomer units such as styrene and its substituted derivatives, acrylic acid or methacrylic acid, alkyl acrylates and methacrylates, hydroxyalkyl acrylates and methacrylates, acrylamides and methacrylamides, vinylpyridine and its substituted derivatives, divinylbenzene, divinylpyridine, alkylene diacrylate, alkylene dimethacrylate, oligoethylene glycol diacrylate and oligoethylene glycol dimethacrylate with up to 5 ethylene glycol repeat units, alkylene bis(acrylamides), piperidine bis(acrylamide), trimethylolpropane triacrylate, trimethylolpropane trimethacrylate, pentaerythriol triacrylate and tetraacrylate, and mixture thereof. It also relates to carbohydrate polymers such as agarose, cellulose, dextran, chitosan, and crosslinked derivatives thereof. As disclosed in more detail below, such organic resin constitutes the core member of the sorbent of the present invention.

As disclosed herein, the term "zwitterionic non-aromatic group" relates to an attached ionic functional non-aromatic group comprising simultaneous positive and negative charges in the same pendant moiety, resulting in lack of net charge under the conditions prevailing during its use. Such groups can exist as monomeric units directly attached to the backbone polymer, or as linear or crosslinked polymeric or copolymeric layers comprised at least partly of non-aromatic zwitterionic monomer units, resulting in multiple zwitterionic non-aromatic groups in each attached moiety pendant to the backbone polymer. Zwitterionic non-aromatic groups are distinguished as "strong" or "weak" depending on whether the ionic non-aromatic group is capable of undergoing a dissociation or protonation equilibria in the aqueous pH range applicable to separation of biological macromolecules. Examples of strong ionic non-aromatic groups are sulfonic acid and quaternary ammonium groups, whereas examples of weak ionic groups are carboxylic acid and alkyl- or hydroxyalkylamine. Examples of strong/strong zwitterionic non-aromatic groups are sulfoalkylammoniobetaines, sulfoalkylarsenobetaines, phosphonoalkylammoniobetaines, and phosphonoalkylarsenobetaines. Weak/strong non-aromatic zwitterions comprise one strong and one weak charge, which means that the net charge can be either zero, in which case the group is zwitterionic, or positive or negative, depending on whether the weak group is protonated or is dissociated into an anionic group, or exists in its neutral form. Weak/weak zwitterionic groups can be exemplified by a) neutral side chain α-amino acids attached through alkylative coupling with the α-amino group, or b) α-protected amino acids attached through a reactive group residing on the side chain producing an uncharged covalent bond, after which the α-amino group is deprotected; both cases constituting amphoteric pendant moieties that can have positive, negative or no net charge, depending on the surrounding pH. In the state of no net charge, these groups which are dissociable or capable of being protonated exist in an equilibrium between doubly oppositely charged zwitterions and the neutral/neutral, non-zwitterionic form. Examples of vinylic monomers with covalently attached strong-strong non-aromatic zwitterionic groups are 3-(2-acrylamido-2-methylpropanedimethylammonio)-1-propanesulfonate, 4-(2-acrylamido-2-methylpropanedimethylammonio)-1-butanesulfonate, 2-Methacryloyloxyethyl phosphorylcholine, 4-[(2-acrylamido-2-methylpropyl)dimethylammonio]butanoate, and 3-[N-decyl,N-(2-methacryloyloxyethyl)N-methyl]ammoniopropanesulfonate. In the following, such polymerizable monomers comprising non-aromatic zwitterionic groups are referred to herein as "zwitterionic monomers". Likewise, a porous sorbent according to the present invention comprising non-aromatic zwitterionic groups is referred to herein as a "porous zwitterionic sorbent".

DETAILED DESCRIPTION OF THE INVENTION

Thus, more specifically, the present invention relates to a novel sorbent, which is especially suitable for use as a stationary phase in a chromatography column. The core of said sorbent consists of an organic polymer carrier of synthetic or natural origin and said carrier exhibits a plurality of covalently bonded non-aromatic zwitterionic groups on the surface thereof. The choice of polymer/copolymer is not critical, and accordingly it is possible to carry out the invention using many different kinds of organic resins. The electrostatic barrier presented by dense zwitterionic functionalization of the surface shields the underlying carrier from interactions with biological macromolecules. The role of the organic resin is thus mainly to act as a mechanically stable carrier for the non-aromatic zwitterionic groups of the present invention. The choice of polymer/copolymer is therefore not important, as long as the selected organic resin has reactive groups available on the surface that will enable attachment using any of the chemistries demonstrated in the examples below. Accordingly, it is possible to carry out the invention by attaching non-aromatic zwitterionic pendant moieties to many different kinds of organic resins.

In a particular embodiment of the invention, a non-aromatic zwitterionic monomer can also be included among the monomers constituting the organic resin sorbent carrier, which thus becomes a porous zwitterionic sorbent per se.

In a specific embodiment thereof, the sorbent carrier according to the invention is porous. More specifically, the pore diameters may range from 0.01 to 10 μm, most preferably having a significant fraction of the pores in the size range from 0.5 to 5 μm, in order to provide a bulk flow path for the eluting solution.

In one embodiment of this first aspect of the invention, the zwitterionic non-aromatic groups have been bound to the surface of the carrier by any suitable metod of polymerisation known to those of skill in the field, preferably by graft polymerisation, of monomers comprising non-aromatic zwitterionic groups. In a particular embodiment, the zwitterionic non-aromatic groups have been incorporated throughout the structure of the carrier sorbent by polymerising monomers comprising non-aromatic zwitterionic groups together with suitable crosslinking monomers easily chosen by someone skilled in the field. More specifically, the zwitterionic non-aromatic groups may have been bound to the carrier by activation with an alkylating functional group, which is subsequently reacted with a ω-dialkylaminoalkylsulfonic acid to form non-aromatic zwitterionic groups on the carrier; likewise, surface-attached non-aromatic zwitterionic pendant groups can be obtained through incorporation of a dialkyl amine, optionally containing hydroxyl groups in either or both alkyl substituents, onto a suitably activated sorbent carrier, followed by reaction with an alkyl sulfone, using reactions known to those of skill in the field. In a particular embodiment, the sorbent carrier is a porous polymeric monolith. In the present context, it is to be understood that the term "a zwitterionic non-aromatic group" relates to a functional group attached to the organic resin carrier as a single identifiable pendant moiety, said functional group being characterized in containing both a negative and a positive ionic charge, incorporated on the organic resin carrier either through a reaction encompassing an existing functional group on the organic resin carrier, directly or after activation, or by polymerizing a monomer containing a functional group with these properties onto the carrier. In another embodiment of the first aspect of the invention, the sorbent carrier is characterised in that the surface of the organic resin has been activated by incorporation of a suitable reactive functional group, such as epoxy, or halogenoalkyl, such as choroalkyl or bromoalkyl and that is capable of alkylating the amino group of an aminoalkylsulfonic acid in a reaction producing covalently bonded zwitterionic non-aromatic groups on the sorbent carrier.

In an advantageous embodiment of the invention, the zwitterionic groups resulting from this reaction are ω-sulfoalkyl-trialkylammonio (sulfobetaine) groups, where at least one of the alkyl substituents of the ammonio group is covalently bonded to the sorbent carrier, and where any or both of the remaining alkyl group can carry a hydroxyl function.

Further, analogous to Example 3 below and using chemical reactions well known to those skilled in the field, the incorporation of a zwitterionic group onto a sorbent carrier can also be accomplished by incorporating a dialkyl amine, optionally containing hydroxyl groups in either or both alkyl substituents, onto a suitably activated sorbent carrier such as, e.g., that produced in Example 2, see below, using known reactions. The sorbent carrier thus functionalized with a disubstituted amine is thereafter reacted with an alkyl sultone, to accomplish a quarternizing sulfoalkylation of the substituted amine. This reaction results in formation of sulfobetaine zwitterions that are attached to the sorbent carrier as pendant moieties, as represented in FIG. 1B. These are the reactions that have been used to produce the zwitterionic monomers used in Examples 5, 6 and 8 presented below to prepare zwitterionic sorbents, whose utility in the separation of biological macromolecules are demonstrated in Examples 9, 10, 12 through 14 below.

Accordingly, the present invention relates to a novel sorbent, which due to the advantageous zwitterionic groups is superior to the prior art methods. More specifically, as compared to the works cited above, it is apparent that in the prior art, alongside anion exchange and cation exchange, there exists a practice termed mixed mode ion exchange, which can be used for separation of proteins. However, due to spatial separation between the cationic and anionic groups, and the difficulty of achieving a stoichiometric balance between said ionic groups, mixed mode ion exchange sorbents are inferior to a true zwitterionic sorbent according to the present invention, wherein the anion and cation exchange groups are incorporated in close proximity on the same pendant functional group.

In accordance with a further observation made by the present inventors, the low retention seen in Example 12 below for the acidic proteins can be due to steric hindrance between large molecules and the zwitterionic sorbent, limiting the access to the quaternary ammonium groups situated in the attaching chains of the pendant zwitterionic moieties reaching into solution. The result will conceptually be an "overexpression" of the cation exchange properties of the zwitterionic group, as the functional group protruding into the solution is the sulfonic acid. Thus, in an additional embodiment of the invention, zwitterionic pendant moieties having their ionic groups attached to the polymeric backbone through linkage with a hydroxyl group residing on the alkyl spacer connecting the anion and cation exchange groups of the zwitterion, may advantageously be used. These "laterally attached" zwitterionic separation materials will be prepared from new zwitterionic monomers, which may be synthesized by quarternization of aminoalkylsulfonic acid type zwitterionic biological buffers having a hydroxyl or similar reactive group in the alkyl spacer interconnecting the ionic groups (for a listing of suitable substrates see, e.g., Sigma Chemical Company, St. Louis, USA; 1995 Catalog, p. 1685–1691), followed by covalently connecting a vinylic monomer to the zwitterionic intermediate through the reactive group in the interconnecting alkyl chain, based on the formation of linkage such as an amide, ester, ether, according to principles known to those skilled in the field. Polymerization of this monomer either as a copolymer or in a grafting process will result in a zwitterionic sorbent. In this sorbent the pendant zwitterionic moiety will be attached to the polymeric carrier, not through the quarternary ammonium group, but through the reactive group in the alkyl chain interconnecting the ionic groups, thereby simultaneously exposing both ionic charges of the pendant zwitterionic group to the external solution in a lateral fashion. Accordingly, applying similar covalent attachment chemistries, zwitterionic intermediates may be attached in a lateral fashion to porous polymer substrates having functional groups suitable for forming a covalent link with a reactive group in the alkyl spacer interconnecting the ionic groups of the zwitterion.

In second aspect, the present invention relates to a method for purifying a particular biological macromolecule, such as a protein or a nucleic acid, by zwitterionic ion exchange chromatography, comprising the steps of
  a) determining the appoximative net charge of the biological macromolecule in aqueous solution as a function of the pH of said solution;
  b) using the information obtained in step a) for choosing a pH and an ionic strength at which the macromolecule obtains an interaction of an appropriate strength with a zwitterionic ion exchange column;
  c) using the information obtained in step b) for choosing a pH and an ionic strength of the isocratic eluting solution or the eluting solution gradient composition with which the macromolecule is eluted;
  d) applying a solution containing said biological macromolecule to a separation column comprising zwitterionic sorbent carriers, said solution having a pH and an ionic strength that have been chosen in step b);

e) eluting the separation column in step d) with an elution solution whose pH and ionic strength have been chosen in step c); and f) recovering said biological macromolecule.

Most preferably, the zwitterionic sorbent carriers are any of the advantageous embodiments of the invention as defined above.

In a particular embodiment of the present method, the maximum ionic strength used is 0.25 M. Those skilled in this field may easily choose a suitable value depending on the prevailing conditions at the time.

As regards the solvent in the elution solution, it may advantageously consist of water with less than 10% admixture of an organic solvent, which is chosen as appropriate by someone with skills in this field.

In a further aspect, the present invention relates to an ion exchange column suitable for use in zwitterionic ion exchange chromatography comprising a sorbent carrier according to the present invention.

In summary, the present invention discloses three fundamentally different ways for the preparation of porous polymeric sorbents materials with zwitterionic functional groups existing as separately identifiable pendant entities on their surface, and demonstrates the utility of these sorbent materials in a novel separation column chromatographic process for analysis and purification of biological macromolecules. The three different synthesis routesaccording to the invention are; a) direct co-polymerization of zwitterionic monomers yielding zwitterionic sorbents; b) incorporation of zwitterionic groups onto existing porous polymeric sorbent carriers (two different routes are devised); and c) graft polymerization of zwitterionic monomers onto sorbent carriers. Zwitterionic sorbents prepared according to all three routes are capable of separating biological macromolecules under particularly mild and totally aqueous conditions based upon electrostatic interactions, as exemplified for many different proteins and peptides.

DETAILED DESCRIPTION OF THE DRAWINGS

Figure 2:
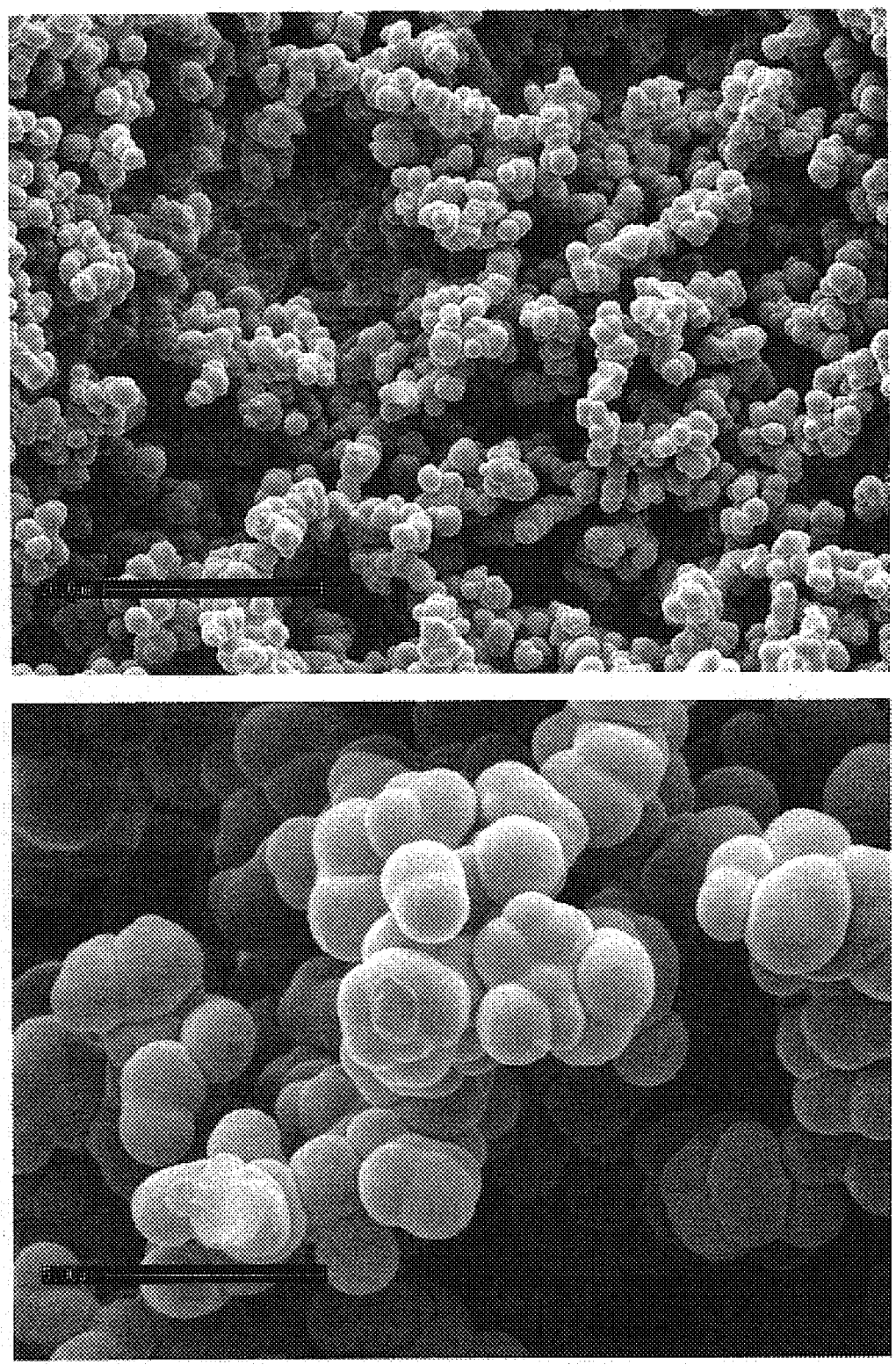
FIGS. 2*a* and *b* show scanning electron micrographs of a photopolymerized zwitterionic monolith.
Figure 3:
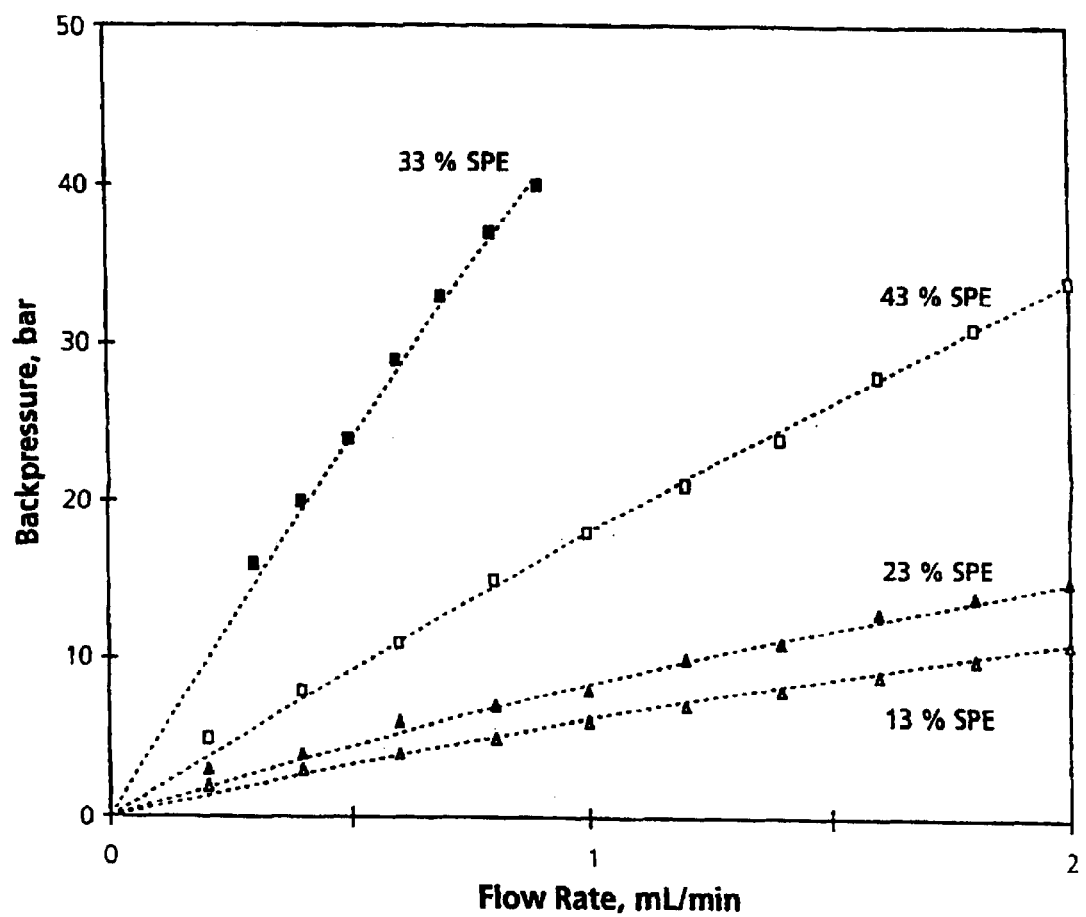
FIG. 3 presents back pressure vs. flow rate in water for SPE-copoly-TEGDMA based monoliths prepared using varying SPE:TEGDMA ratios.
Figure 4:
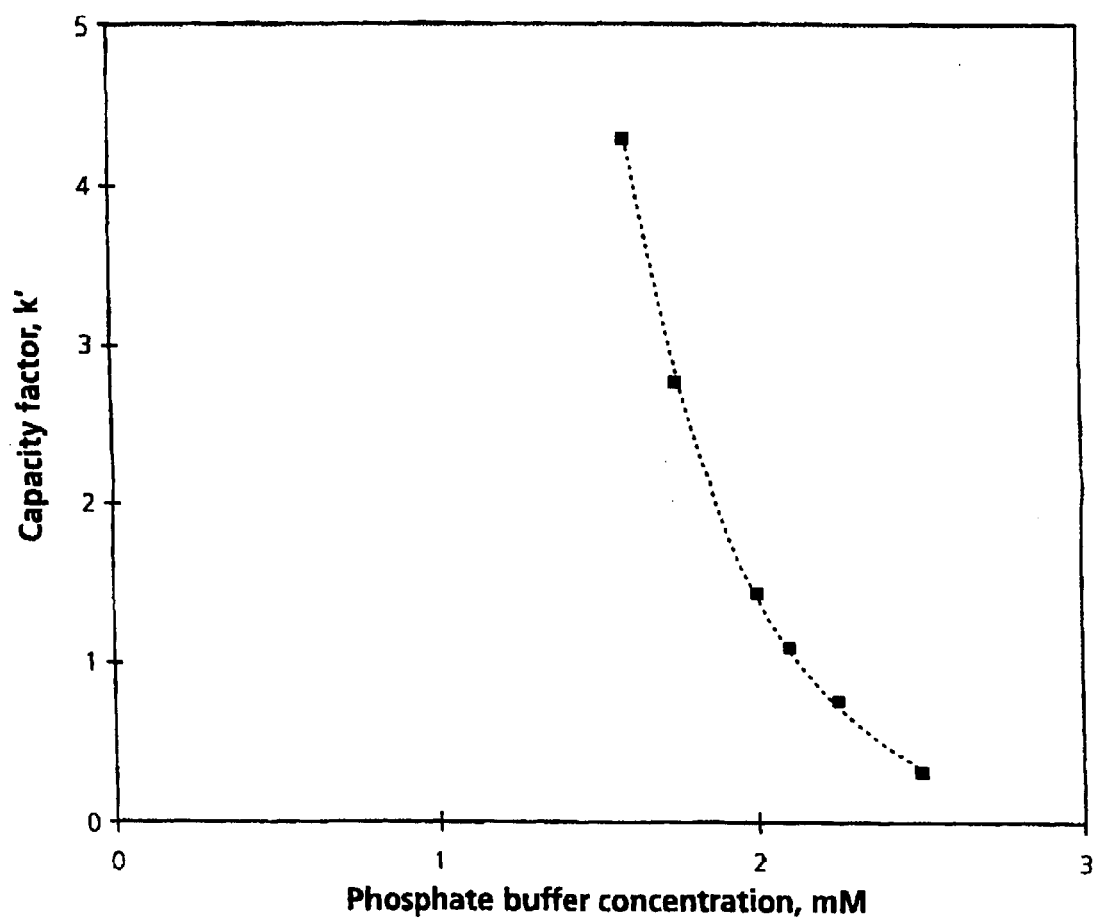
FIG. 4 discloses the dependency of lysozyme retention on the mobile phase ionic strength for a SPE-copoly-TEGDMA monolith.
Figure 5:
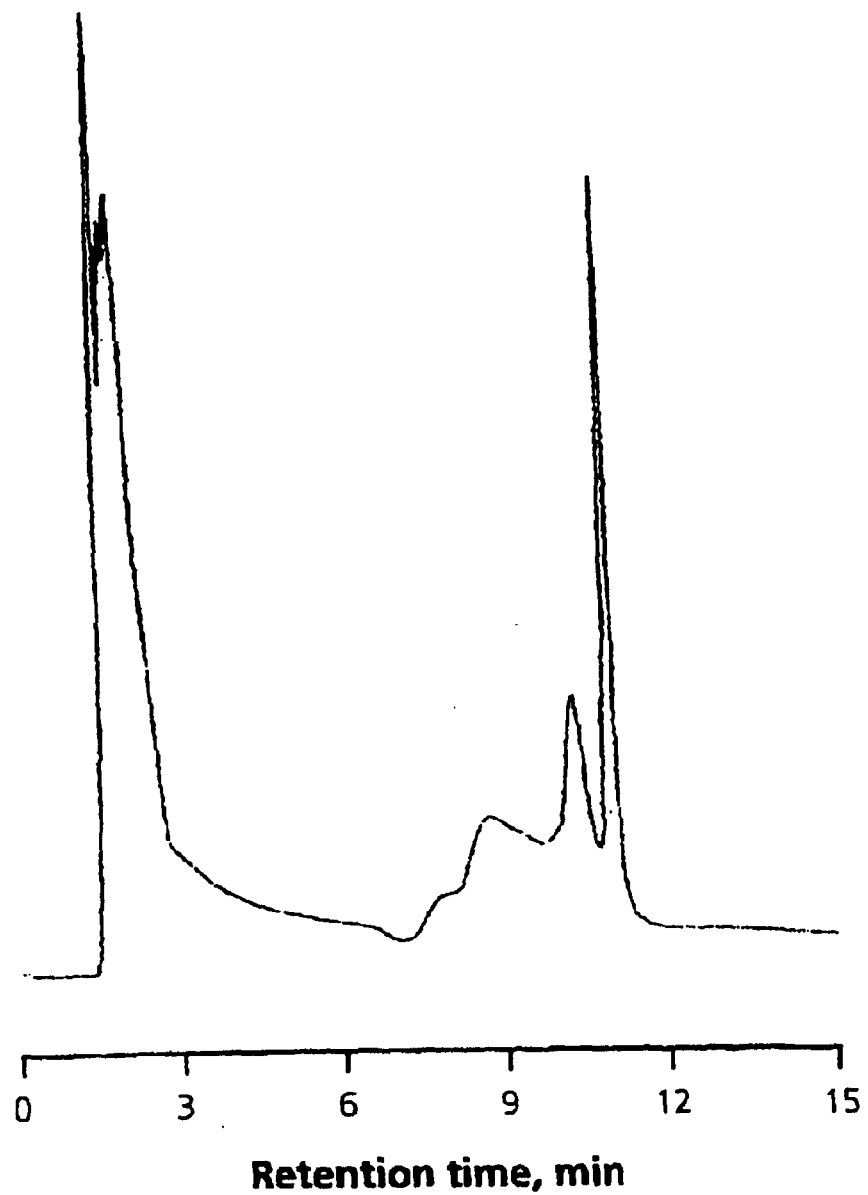
FIG. 5 shows the purification of a partly purified protein extract containing an unknown amount of biologically active antibacterial peptides.
Figure 6:
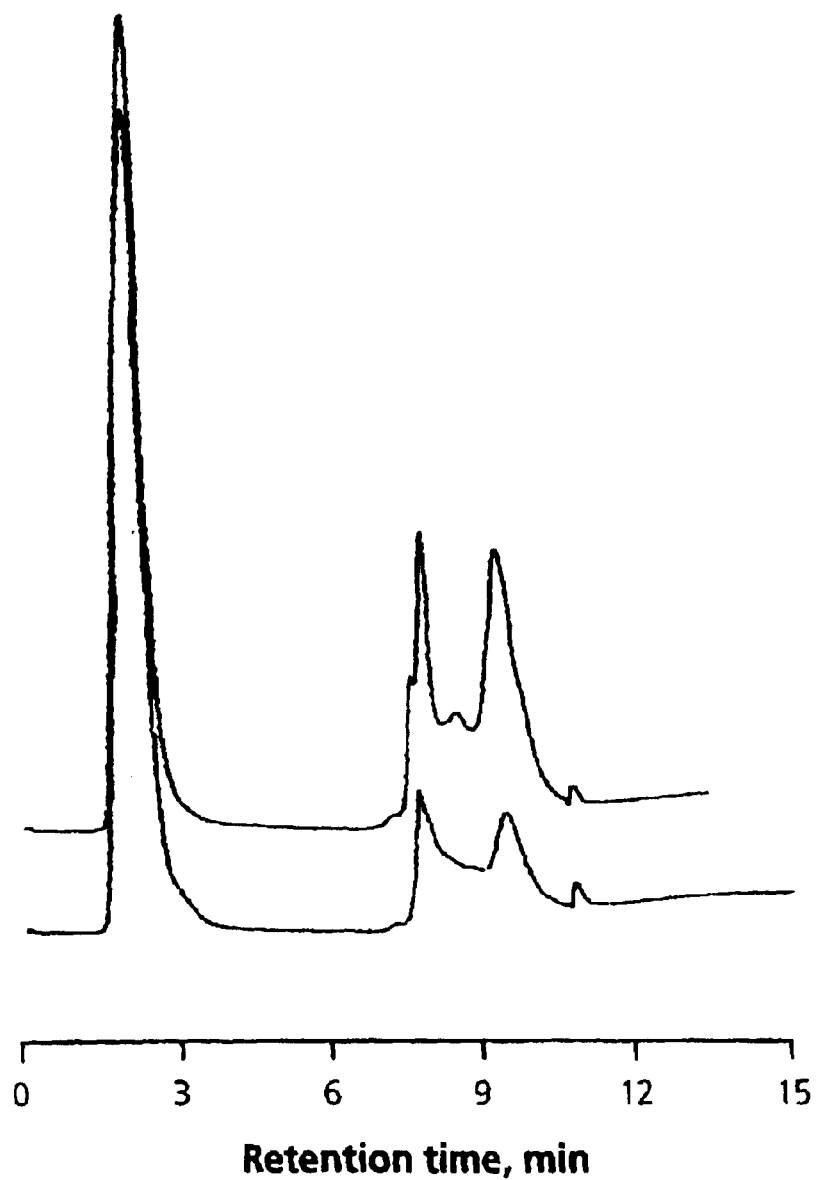
FIG. 6 relates to purification the synthetic peptides A (upper trace) and B (lower trace), as disclosed in Example 10 below.
Figure 7:
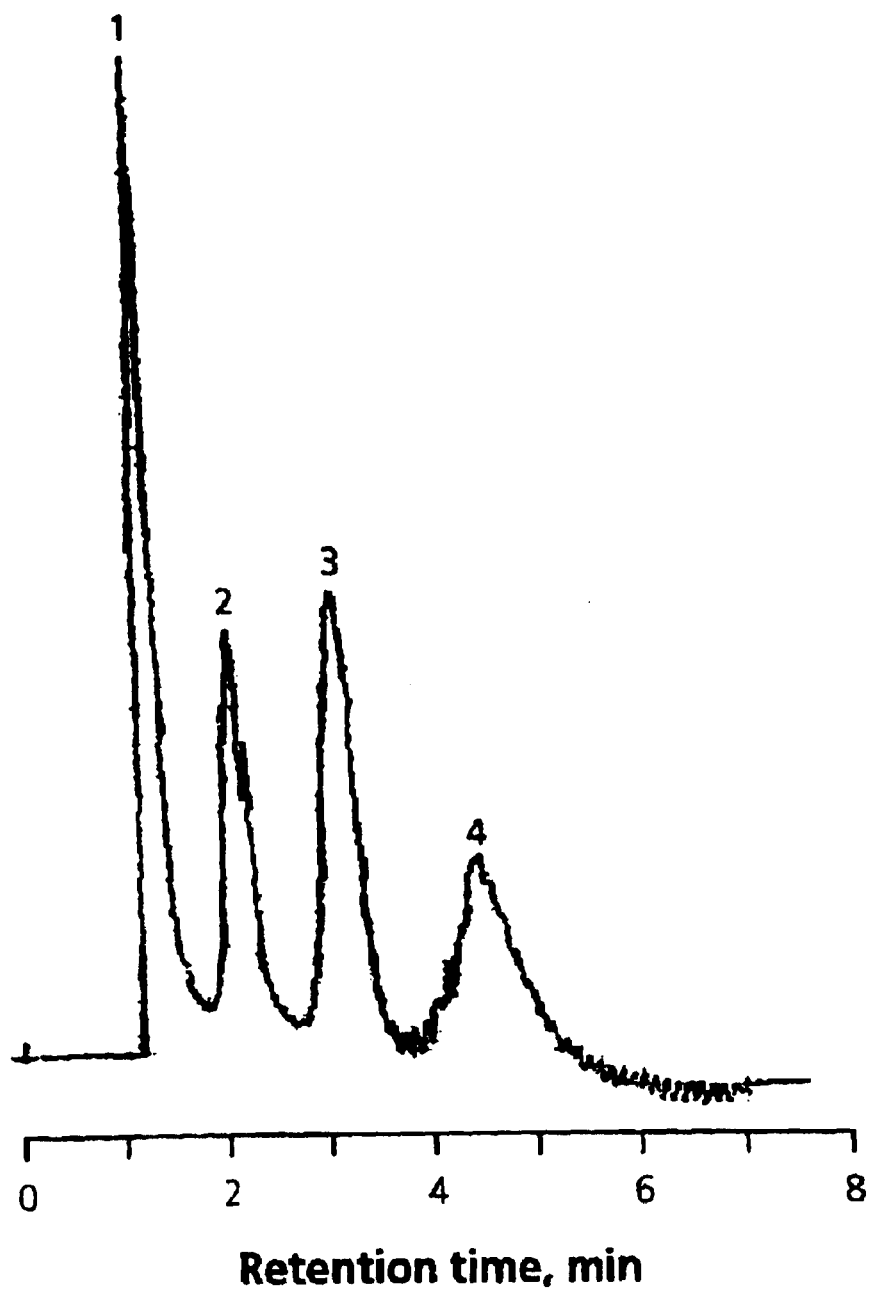
FIG. 7 shows a separation of myoglobin (1), ovalbumin (2), cytochrome C (3) and lysozyme (4) on a zwitterionic column according to the present invention.
Figure 8:
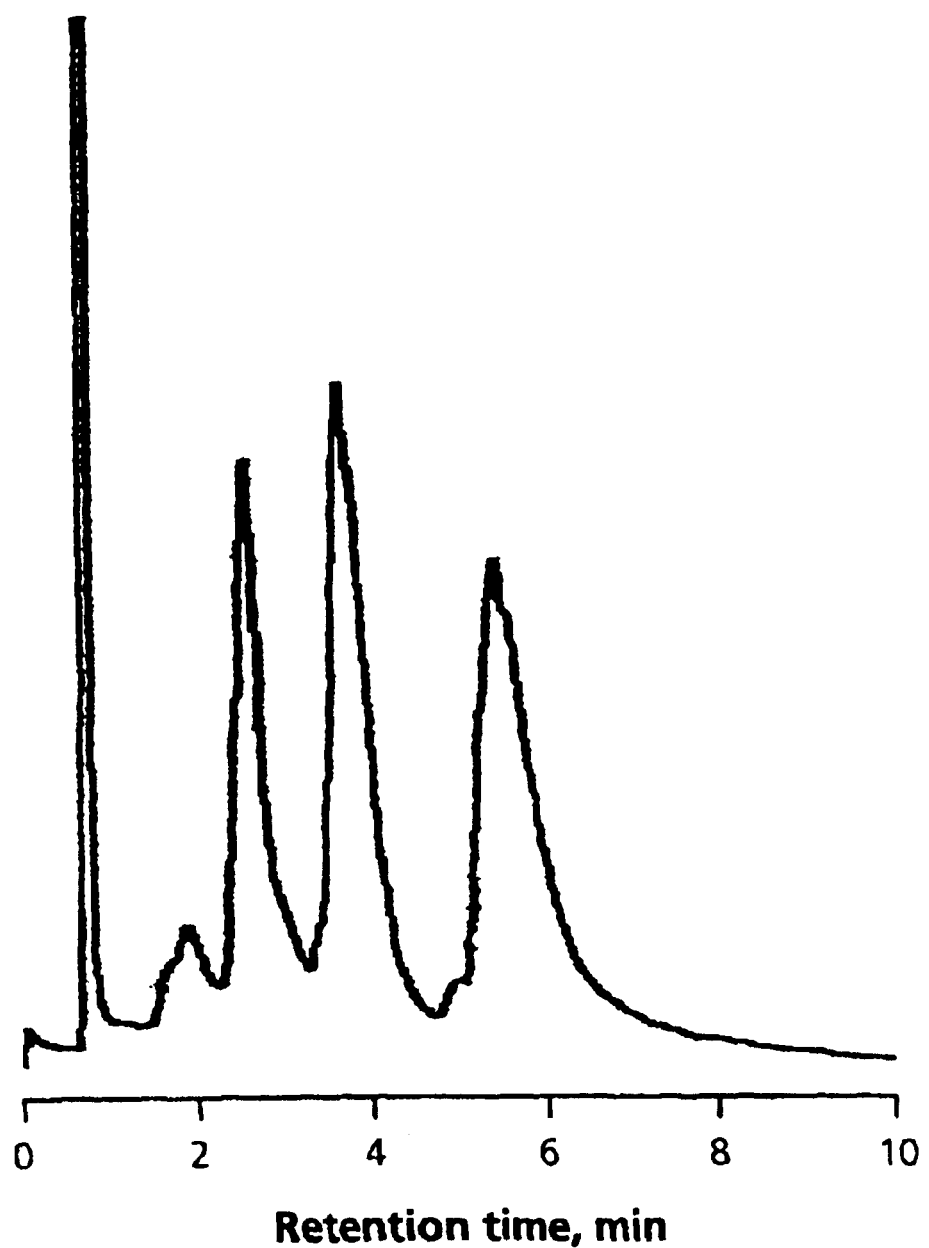
FIG. 8 presents separation of a 5 $\mu$L injection of a protein mixture containing 0.5 mg/mL each of (from left to right)
Figure 9:
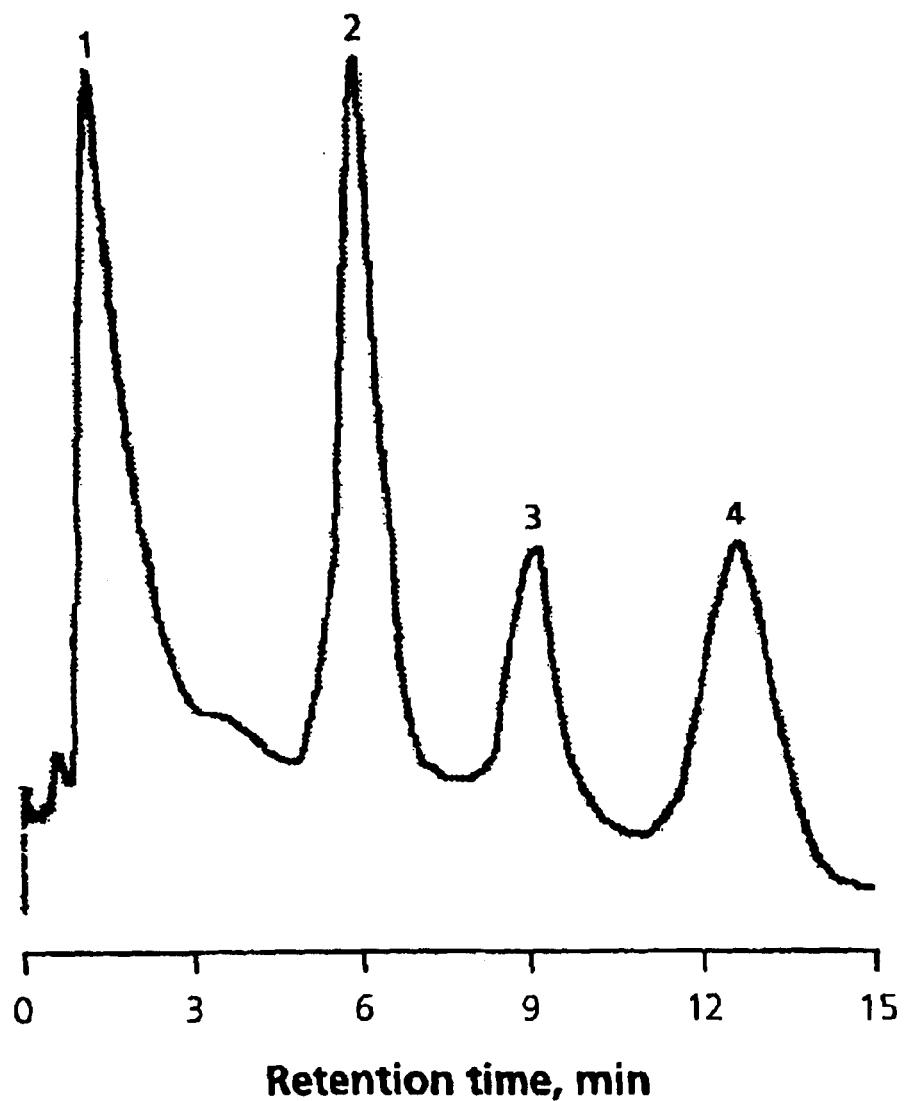
FIG. 9 shows the separation of the proteins ovalbumin (1), conalbumin (2), α-chymotrypsinogen A (3) and cytochrome C (4) on a grafted monolith according to the invention.

The present invention will now be described with reference to the enclosed figures in which:

FIG. 1 shows schematic representations of A) the activation and functionalization reactions carried out according to Examples 2–4 below and B) a zwitterionic functionalization reaction based on chemical reactions known to those skilled in the field, that will result in zwitterionic sorbents useful for practising the invention; FIG. 2a and b shows scanning electron micrographs of a photopolymerized zwitterionic monolith comprising non-aromatic zwitterionic groups (at two different magnifications denoted 2a and 2b, indicated by the bar in each picture) prepared from 3 parts of monomer containing 43% SPE and 57% TEGDMA, mixed with 7 parts of methanol and 1% benzoin methyl ether (with respect to the weight of the monomers), photopolymerized at 360 nm for 1 hour;

FIG. 3 presents back pressure vs. flow rate in water for SPE-copoly-TEGDMA based monoliths prepared using varying SPE:TEGDMA ratios, as disclosed in Example 5 below;

FIG. 4 discloses the dependency of lysozyme retention on the mobile phase ionic strength for a SPE-copoly-TEGDMA monolith prepared according to Example 6 below;

FIG. 5 shows the purification of a partly purified protein extract containing an unknown amount of biologically active antibacterial peptides on a column as described in Example 9 below;

FIG. 6 relates to purification the synthetic peptides A (upper trace) and B (lower trace), as disclosed in Example 10 below;

FIG. 7 shows a separation of myoglobin (1), ovalbumin (2), cytochrome C (3) and lysozyme (4) on the zwitterionic column according to Example 11 below;

FIG. 8 presents separation of a 5 μL injection of a protein mixture containing 0.5 mg/mL each of (from left to right) myoglobin, α-chymotrypsinogen A, cytochrome C and lysozyme on column as described in Example 12 at 1 ml/min flow rate of the eluent (a linear gradient from 0.5 to 2.5 mM phosphate buffer, pH 7) in 9 minutes using UV spectroscopic detection at 280 nm; and FIG. 9 shows the separation of the proteins ovalbumin (1), conalbumin (2), α-chymotrypsinogen A (3) and cytochrome C (4) on the grafted monolith prepared according to Example 8; and practiced according to Example 13.

EXPERIMENTAL

Materials and Methods

The following general methods and materials were used in the experimental work described below:

a) Reagents and Solutions

The zwitterionic monomer N,N-dimethyl-N-methacryloxyethyl-N-(3-sulfopropyl) ammonium betaine (SPE) was obtained from Raschig AG, Germany, and was used without further purification. Ethylene dimethacrylate (EDMA, 90%) was purchased from Fluka A G, Buchs, Switzerland, while triethylene glycol dimethacrylate (TEGDMA, 95%) and benzoin methyl ether (99%) were obtained from Aldrich, Steinheim, Germany, and the methanol was of analyzed HPLC grade (J. T Baker, Deventer, Holland).

Proteins used as probes in the chromatographic experiments were all purchased from Sigma. The synthetic peptides used to produce FIG. 8 were specified as having molecular weights of 2712 g/mol (a) and 2669 g/mol (b), and the peptide purities were determined by HPLC to >95% and >97%, respectively. The sequences of the peptides differ only with respect to one amino acid (phenylalanine and cysteine, respectively) underlined in the sequences below:

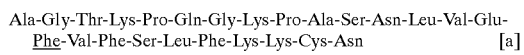

Ala-Gly-Thr-Lys-Pro-Gln-Gly-Lys-Pro-Ala-Ser-Asn-Leu-Val-Glu-Phe-Val-Phe-Ser-Leu-Phe-Lys-Lys-Cys-Asn    [a]

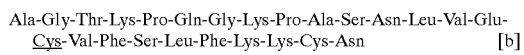

Ala-Gly-Thr-Lys-Pro-Gln-Gly-Lys-Pro-Ala-Ser-Asn-Leu-Val-Glu-Cys-Val-Phe-Ser-Leu-Phe-Lys-Lys-Cys-Asn    [b]

The biological peptide preparation used to prepare FIG. 9 was obtained as a crude extract from the Laboratory of Microbial Gene Technology, NLH, Ås, Norway, and was roughly purified using a Sephadex cation exchanger (Pharmacia) followed by hydrophobic interaction purification. The sample was finally obtained in an aqueous 70% ethanol solution.

b) Photopolymerization

The poly(SPE-co-TEGDMA and the poly(SPE-co-EDMA) monoliths were generally prepared by dissolving the SPE monomer and the benzoin methyl ether (photoinitiator) in methanol, followed by addition of the crosslinker (TEGDMA or EDMA). Each polymerization mixture was sonicated for 10 minutes and purged with helium for 10 minutes. The glass columns (150 or 250 mm long by 2.3 mm i.d.) were surface treated with a silanization procedure to produce pendant 3-methacryloyloxypropyl anchoring groups attached to the inner surface. The photopolymerizations were carried out with the sealed glass columns positioned vertically for 60 minutes using a Spectrolinker XL 1500 UV (Spectronics Corp., Westbury, N.Y.) with eight 15 W fluorescent blacklight tubes (F15T8/BLB; GTE Sylvania), producing UV light of predominately 365 mm wavelength. Reference samples for SEM analysis were polymerized in polypropylene tubes (4 mm i.d.) for comparison purposes.

After completion of the polymerization, each column was furnished with fittings, connected to an LC system and soluble compounds still remaining in the monolith were washed out using water as the mobile phase.

c) Chromatography

Chromatography of proteins was carried out using an HPLC system consisting of two LDC (Laboratory Data Control, Riviera Beach, Fla.) Constrametric pumps and an LDC Constrametric variable wavelength UV detector. The samples were injected through a Rheodyne (Cotati, Calif.) loop injector with internal wetted parts made from poly (ether-ether-ketone) and data were collected using a Hewlett Packard (Palo Alto, Calif.) HP3396A integrator. Separations of model proteins were carried out at according to the conditions indicated in each Figure.

Peptide purification chromatography was carried out using a Spectra-Physics (Mountain View, Calif.) Spectra-SYSTEM P400, provided with a Spectrafocus forward optical scanning detector.

d) Characterization of the Zwitterionic Polymer

Prior to scanning electron microscopy study, the polymer samples were placed on sticky carbon foils which were attached to standard aluminum specimen stubs. The samples were coated with approximately 20 nm of gold by using a combination of sputter coating (Edwards S150A Sputter Coating Unit, Edwards High Vacuum, incorporating an automatic tilting and rotation device). Microscopic analysis of all samples was carried out in a S360 iXP SEM (Leica Cambridge Ltd., Cambridge; UK) operated in LaB$_6$-mode, 5 kV, 100 pA probe current and 0° tilt angle.

The sulfur and nitrogen contents were determined by elemental analysis of crushed samples using a Leco SC 432 (Leco, St. Joseph, Mich.) in order to verify the compositions of the zwitterionic polymers.

The present invention will now be further described with reference to the enclosed examples, which are included for the purpose of illustration and are not intended to limit the scope of the appended claims. All references cited below or elsewhere in this application are hereby included herein by reference.

EXAMPLE 1

Synthesis of 2-Dimethtylaminothanesulfonic Acid (DMAES)

2-Bromoethylsulfonic acid sodium salt (10.88 g; 0.05 mol) was dissolved in 100 mL of water in a 250 mL E-flask. Dimethylamine (12.40 g, 0.11 mol) was added to above solution, and the mixture was allowed to stand for 45 minutes at room temperature and then reacted at 70–80 °C. for 18 hours under refluxing conditions. After cooling the solution to 40 °C., approx. 2 g granulated charcoal was added, and the mixture was boiled for 15 minutes without a refluxing condenser. The mixture was cooled to room temperature, the charcoal was allowed to settle and the supernatant solution was thereafter filtered (Whatman GF/A) under weak suction. Further purification was carried out by letting the solution pass through a 150 mm×40 mm i.d. glass column packed with Dowex 350 UPN (Dow Chemical, Midland, Mich.) sulfonic acid strong cation exchanger in the H$^+$ form at a flow rate of approx. 2 mL/min. The purified solution was precipitated twice from boiling water/ethanol and dried at 50 °C. for 24 hours in a vacuum oven. The purity of the DMAES was determined by $^1$H NMR (400 MHz, Bruker) using D$_2$O as solvent ($\delta$=2.3 ppm [2H, —CH$_2$—]; $\delta$=2.5 ppm [2H, —CH$_2$—]; $\delta$=1.9 ppm [6H, (CH$_3$)$_2$—N]).

EXAMPLE 2

Activation of Hydroxyethyl Functional Particles with Epoxy Groups

Five grams of 12 μm diameter Spheron 300 crosslinked porous polymer beads (a product based on 2-hydroxyethyl methacrylate as active groups; purchased from Chemapol, Brno, Czech Republic) were suspended in 30 mL of 50% aqueous NaOH in a 100 mL ground-neck flask and stirred for about 1 hour at room temperature until a uniform suspension was obtained. The resulting suspension was kept for 18 hours below 10° C., whereafter ten milliliters of dioxane was added to the flask under slow stirring for 30 minutes at room temperature. A mixture of 25 mL epichlorohydrin and 15 mL dioxane was then filled into the flask, and the activation was allowed to take place under slow stirring for 2 hours at 40° C., then for an additional 2 hours at 60° C. The thus activated particles were filtered on a glass filter and washed to neutral conditions with a large quantity of Milli-Q water, then with methanol (3×100 mL), acetone (3×100 mL), and finally dried for 18 h at 40° C. in a vacuum oven.

EXAMPLE 3

Zwitterionic Functionalization of Epoxy Activated Hydroxyethyl Particles

FIG. 1A relates a schematic representation of the functionalization reaction disclosed in this Example, based on activation of a hydroxy-containing sorbent carrier according to Example 2. To practice this principle, DMAES (2 g; 0.013 mol; prepared according to Example 1) was dissolved in 20 mL of aqueous 0.2 mM phosphate buffer (pH 8) in a 50 mL glass tube. The mixture was thereafter adjusted to pH 8 with 5 M NaOH under stirring. Two grams of epoxy activated polymer beads prepared according to Example 2 were added to the solution under slow stirring and reacted at 50° C. for 90 hours. The reacted beads were thereafter washed with water, methanol, and acetone on a glass filter under weak suction, and finally dried at 50° C. for 18 h in a vacuum oven. These particles were subsequently packed in a 150 mm long by 4 mm i.d. and column used for protein separation, as disclosed in Example 11.

EXAMPLE 4

Zwitterionic Functionalization of Polymer Particles Prepared with an Epoxy-Containing Co-Monomer The reaction in this Example can be schematically represented by the functionalization reaction shown in the second part of FIG. 1A, and was practised on porous polymer particles prepared from a monolith precursor mixture containing 24% (w/w) 2,3-epoxypropyl methacrylate (GMA), 16% ethylene dimethacrylate (EDMA), 54% cyclohexanol and 6% 1-dodecanol. To this mixture, which had been deaerated by purging with helium for 10 minutes, was added 0.4% (w/w) α,α'-azoisobutyronitrile shortly before polymerization, which took place in sealed glass tube molds at 60° C. for 16 hours. The resulting monolithic polymer structure was thereafter removed from the mold by breaking the glass, cut in cubic pieces of approximately 2–3 mm sides, and then Soxhlet extracted with methanol for 24 hours. The extracted monolith pieces were dried, carefully ground in a mortar and thereafter dry sieved. The particle fraction smaller than 200 mesh (74 μm) was used for functionalization according to the procedure described in Example 3, with the exception that the reaction temperature was 40° C. The apparent hydrophilicity of the particles thus produced was evaluated by wetting the material with water, and it was concluded that the material has a pronounced hydrophilic character after functionalization with zwitterionic groups, compared to the distinct hydrophobic behaviour of the epoxy-containing starting material that had not been reacted with DMAES. Elemental analysis, presented in Table 1, revealed that nitrogen and sulfur were bound to the carrier in the appropriate 1:1 stoichiometric ratio. The material was thus zwitterionic, and the amount of zwitterionic groups incorporated increased as function of the reaction time.

TABLE 1 showing the effect of reaction time on the nitrogen and sulfur contents of zwitterionic particles prepared from a ground and sieved porous GMA-copoly-EDMA monolith, functionalized with DMAES according to Example 4.

| Reaction time h | % $N_{E.A.}$[a] | % $S_{E.A.}$[a] | % $S_{calc.}$[b] | % $S_{E.A.}$:% $S_{calc.}$[c] |
|---|---|---|---|---|
| 40 | 0.16 | 0.37 | 0.37 | 1.00 |
| 90 | 0.22 | 0.49 | 0.50 | 0.98 |

[a]Percent nitrogen determined by elemental analysis; [b]percent sulfur determined by elemental analysis; [c]ratio of percent sulfur determined by elemental analysis to the percentage needed to fulfil a 1:1 stoichiometric n:s ratio. An elemental analysis was also made after 20 hours of reaction, but due to the low amount of groups incorporated after this short reaction time, the value for the % $S_{e.a.}$:% $S_{calc}$ ratio became erroneous.

EXAMPLE 5
Zwitterionic Monolithic Sorbent by Direct Photocopolymerization of SPE with TEGDMA N,N-dimethyl-N-methacryloxyethyl-N-(3-sulfopropyl)-ammonium betaine (SPE) is a crystalline zwitterionic monomer that dissolves readily in water but is insoluble in the crosslinking monomers EDMA and triethyleneglycol dimethacrylate (TEGDMA), and also in most organic solvents known to have been used as porogens in suspension or mold polymerizations. On the other hand, the crosslinking monomers EDMA and TEGDMA are insoluble in water, which presented a compatibility problem in the search for a pore forming solvent capable of dissolving SPE and the crosslinker simultaneously, as well as yielding a macroporosity in the final polymer. We eventually discovered that methanol can serve as solvent for all components included in the mold without risking compatibility problems due to precipitation.

Based on this discovery, a series of SPE-copoly-TEGDMA monoliths were prepared by dissolving the water soluble SPE monomer and 0.1 g of the photoinitiator benzoin methyl ether in 7.0 grams of methanol, followed by addition of TEGDMA. The total weight of SPE and TEGDMA was 3.0 grams in all experiments, while the SPE:TEGDMA weight ratios were 13:87, 23:77, 33:67 and 43:57 in the four different preparations. These mixtures were treated individually in an ultrasonic bath (Bransonic 221) for 10 minutes and thereafter purged with a low flow of helium gas for 10 minutes to remove dissolved oxygen. The degassed mixtures were then filled into separate glass columns (50 or 250 mm long by 2.3 mm i.d.), the inner surfaces of which had been treated with 3-methacryloyloxy-propyl trimethoxysilane according to known procedures to obtain polymerizable anchoring groups on the surface. The contents of the columns was then subjected photopolymerization for 60 minutes by positioning the sealed columns vertically inside a Spectrolinker XL 1500 TV (Spectronics Corp., Westbury, N.Y.) with eight 15 W fluorescent blacklight tubes (F15T8/BLB; GTE Sylvania) as radiation source. Reference samples for SEM analysis were polymerized in 4 mm i.d. polypropylene tubes in a similar manner and used for comparison purposes. After completion of the polymerization, each column was furnished with fittings, connected to an LC system and soluble compounds still remaining in the monolith were washed out with water, whereafter the columns were ready for evaluation as separation media for biological macromolecules, as disclosed in Example 12.

The zwitterionic monolithic sorbents obtained after copolymerization of SPE with TEGDMA were characterized by high levels of porosity and high flow permeabilities. SEM micrographs revealed that a macroporous structure was formed, comprising wide pore channels traversing clusters of nearly spherical units with estimated diameters ranging between 1 to 3 $\mu$m; cf FIG. 2. The high flow permeability of the porous SPE-copoly-TEGDMA based zwitterionic monoliths (cf. FIG. 3) combined with their apparent hydrophilicity indicated their suitability for chromatographic separation of large biomolecules.

EXAMPLE 6
Zwitterionic Monolithic Sorbent by Direct Photocopolymerization of SPE with EDMA Monolithic separation columns were prepared largely according to the procedure described in Example 5, with the significant exception that EDMA was substituted for TEGDMA as crosslinking agent. The polymerization cocktail thus used contained 32 percent by weight of a mixture of 47% SPE and 53% EDMA (w/w) mixed with 68 weight percent of methanol, with 1% benzoin methyl ether (with respect to the weight of the monomers) added. The retention time for the basic and hydrophobic protein lysozyme (0.5 mg/mL, injected through a 5 $\mu$L loop), as function of ionic strength on a 250 mm long by 2.3-mm i.d. column using of a totally aqueous buffer, is presented in FIG. 4. Analogous to the SPE-copoly-TEGDMA zwitterionic monolithic sorbents prepared in Example 5, this SPE-copoly-EDMA zwitterionic monolithic sorbents had a high flow permeability combined with a pronounced apparent hydrophilicity. Their suitability for chromatographic separation of large biomolecules was reduced to practice in the experiments related in Example 12.

EXAMPLE 7
Preparation of Monolithic Grafting Substrates Based on Poly(TRIM)

Sorbent carder materials intended as substrates for grafting of zwitterionic monomers were prepared as monoliths, using a polymerization cocktail containing 40% (w/w) trimethylolpropane trimethacrylate (TRIM) in 60% of a porogen mixture containing 2,2,4-trimethylpentane:toluene 4:1 (w/w). To this cocktail was added 1% (w/w) benzoin methyl ether as polymerization initiator.

Photopolymerization was thereafter carried out following the procedure in Example 5, with the significant exception that 50 mm long columns were used and methanol was used in the washing step. The resulting monolithic sorbent carriers were used for synthesis of a zwitterionic sorbent by graft polymerization of SPE zwitterionic monomer onto its porous structure, as disclosed in Example 8.

EXAMPLE 8
Grafting Zwitterionic Polymeric Layers onto Poly(TRTM) Substrates

Grafting of zwitterionic monomers into the pore system of the poly(TRIM) monolithic sorbent carriers from Example 7 was achieved by filling the monolithic column with a solution containing 10% (w/w) SPE zwitterionic monomer and 0.1% (w/w) potassium peroxodisulfate in water. The grafting solution was delivered to the column from a reservoir consisting of a 1.25 mL loop attached to a sample injector, using a flow rate of 0.2 mL/min. When the column had been filled with the grafting solution, it was sealed and the grafting reaction was allowed to proceed for 20 hours at 70° C. After completion of the reaction, the column was connected to a pump and flushed with 100 mL distilled water, followed by 25 mL of 0.25 M NaCl in order to remove residual monomer and ungrafted homopolymer from the monolithic sorbent. This column resulting from this procedure was used to demonstrate the protein separation disclosed in Example 13.

The choice of a monolithic substrate in this example was made because of the facile way of preparing these carrier substrates, and does not imply that grafting reactions for introduction of zwitterionic layers suitable for practising the invention are restricted to carrier substrates with this confection.

EXAMPLE 9
Purification of a Bacterially Produced Peptide Preparation Using an SPE-Copoly-EDMA Monolithic Zwitterionic Sorbent The applicability of the zwitterionic sorbent prepared in Example 6 was tested for the final purification of a peptide preparation, which had been partly purified by cation exchange on Sephadex followed by hydrophobic interaction chromatography according to known procedures. The peptides in this crude preparation are mainly antibacterial peptides from *Lactobacillus* sp., and are hydrophobic and basic in nature. Existing optimized final purification schemes for these peptides using conventional materials therefore involves reversed phase chromatography with up to 70% isopropanol as eluting solution. A chromatogram showing the purification of 100 µL of partly purified antibacterial peptide extract when injected on the SPE-copoly-EDMA monolithic sorbent as a 70% aqueous ethanol solution is shown in FIG. 5. A linear gradient from pure water to 0.1 M phosphate buffer, pH 7, over 10 minutes was used as eluting solution at a flow rate of 0.7 mL/min. The chromatograms in FIG. 8 are monitored by UV spectroscopic detection at 214 and 280 nm, respectively. Peak identification was done by biological assay, comprising monitoring the antibacterial activity of fractions eluting from the column by applying aliquots on agar plates with indicator bacteria and registering growth inhibition according to known procedures. Strong antibacterial activity was found in the fractions corresponding to the last eluting peaks in the chromatogram. From the UV absorbance, it is clearly seen that a significant amount of non-active proteins or peptides are eluted closer to the void volume.

EXAMPLE 10
Separation of Synthetic Peptides Using as SPE-Copoly-EDMA Monolithic Zwitterionic Sorbent A separation analogous to that demonstrated in Example 9 was done on a pair of synthetic antibacterial peptides with molecular weights 2,712 g/mol (A) and 2,669 g/mol (B), and described by the following amino acid sequences:

Ala-Gly-Thr-Lys-Pro-Gln-Gly-Lys-Pro-Ala-Ser-Asn-Leu-Val-Glu-<u>Phe</u>-Val-Phe-Ser-Leu-Phe-Lys-Lys-Cys-Asn

Ala-Gly-Thr-Lys-Pro-Gln-Gly-Lys-Pro-Ala-Ser-Asn-Leu-Val-Glu-<u>Cys</u>-Val-Phe-Ser-Leu-Phe-Lys-Lys-Cys-Asn

Both peptides are highly basic (pI 9.9) and differing only with respect to one amino acid (phenylalanine and cysteine, respectively) indicated in the sequences above. Twenty microliter of a solution containing 0.68 and 0.8 mg/mL, respectively, of the synthetic peptides A and B in 1% aqueous trifluoroacetic acid was injected on the same column that was used in Example 9, using as eluting solution a linear gradient from pure water to 0.1 M phosphate buffer, pH 7, in 10 minutes at a flow rate of 0.7 mL/min. Detection took place by UV spectroscopy at 214 and 280 nm respectively. Both peptides were retained on the SPE-based resin, and could be eluted using mild conditions, as shown in FIG. 6.

EXAMPLE 11
Protein Separation on a Zwitterionic Sorbent Prepared from Epoxy Activated Hydroxyethyl Particles The column containing zwitterionic sorbent prepared in Example 3 was used for separation of four selected model proteins (myoglobin, ovalbumin, cytochrome C, and lysozyme) using as eluting solution a gradient changing linearly from pure water to 0.1 M NaCl over a period of 10 min at a flow rate of 1 ml/min, detected by UV spectroscopy at 280 nm. The result of this separation is disclosed in FIG. 7. Elution of all proteins was accomplished with a totally aqueous eluting solution consisting of a gradient from pure water to 0.1 M NaCl. Notably, the peak from lysozyme is sharp and symmetric.

EXAMPLE 12
Protein Separation on an SPE-Copoly-EDMA Zwitterionic Monolith

A number of protein probes were injected separately on an SPE-copoly-EDMA monolithic zwitterionic sorbent prepared in Example 6, using water as the eluent. The chromatogram in FIG. 8 shows that a protein mixture containing 0.5 mg/mL each of myoglobin, α-chymotrypsinogen A, cytochrome C and lysozyme could be separated in less than 10 minutes using a totally aqueous eluent having a 2.5 mM phosphate buffer (pH 7) as the only ionic component. The ionic strength required to elute the strongest retained protein is thus in the same range as the ionic strength 1.6 normally used for loading proteins onto conventional cation exchangers [Deutscher, M. P. (Ed.), Guide to Protein Purification (Meth. Enzymol., Vol. 182), Academic Press, 1990]. The zwitterionic separation mode is therefore advantageous for preventing precipitation during separation due to salting out, and for preserving the biological activity of proteins. Furthermore, as the protein elutes in a totally aqueous low ionic strength buffer in the physiological pH range, this process is advantageous in preparative mode separations. Considering the high amount of zwitterionic groups in the tested columns, the interaction between the SPE-copoly-EDMA monolithic zwitterionic sorbent and proteins is of a substantially weaker nature than that seen with ordinary cation or anion exchange resins (used either separately, in tandem, in mixed bed, or in mixed-mode configurations). The SPE-copoly-EDMA zwitterionic monolith is also showing a quite symmetrical peak for the basic enzyme lysozyme (known to be particularly difficult to separate due to its high pI and pronounced hydrophobicity). This separation was achieved without having to resort to extreme eluting conditions, such as, e.g., the combined use of a pH gradient from pH 5 to pH 8 in combination with 1 M ionic strength in the elution solution, as required with the mixed-mode media described by Kurganov et al., containing both cation and anion exchange sites spatially separated on the same carrier (Kurganov, A. A.; Davankov, V. A.; Unger, K. K., J. Chromatogr., 1991, 548, p. 212 and FIG. 5 contained in this reference).

EXAMPLE 13
Protein Separation on an SPE Grafted TRIM Monolith

The monolithic zwitterionic sorbent prepared by grafting of SPE onto a TRIM-based monolithic sorbent carrier in Example 8 was used as a separation column for a protein test mixture containing as test probes the acidic proteins ovalbumin and conalbumin, and the basic proteins α-chymotrypsinogen A and cytochrome C, injected on the column as a 20 μL sample containing of 1 mg/mL of each protein. The eluting solution was a gradient consisting from 0 to 2 min after the injection of 100% water, and from 2–12 min of a linear gradient from water to 0.15 M $NaClO_4$, pumped at a flow rate of 0.5 mL/min. Detection took place by UV spectroscopy at 280 nm.

The separation of acidic and basic proteins in the same chromatogram, as shown in FIG. 9, cannot be carried out on an ion exchange sorbent containing only anion exchange or cation exchange groups. The symmetric shape of the curves demonstrates a very low unspecific binding of the proteins to the grafted zwitterionic sorbent, indicative of advantageous kinetics in the chromatographic retention process. The higher eluent strength needed on this grafted sorbent, as compared to an SPE-copoly-EDMA monolithic sorbent having zwitterionic monomer as part of its basic composition (cf. Example 12) or a particulate sorbent with zwitterionic pendant moieties reacted onto its surface (cf. Example 11; when comparing the elution conditions it must be noted that perchlorate is substantially more effective as eluting ion compared to the chloride ion) reflects an increased availability of the grafted zwitterionic chains to the proteins, most probably due to the extension of the graft chains into solution, in combination with the absence of crosslinking in the grafted layer. It is thus apparent from Examples 11–13, that the retentive strength of the zwitterionic separation sorbents vis-a-vis proteins can be varied within a wide range by either a) incorporation of zwitterionic monomers in the polymerization, mixture leading to the polymeric carrier substrate, which thus becomes a zwitterionic sorbent without further functionalization reactions; b) functionalizing the sorbent carrier surface with zwitterionic groups, c) attaching zwitterionic grafts of varying length to the sorbent carrier surface; or any combination thereof.

EXAMPLE 14
Determination of Protein Recovery on Zwitterionic Separation Materials Non-specific interactions between proteins and sorbents constituting chromatographic stationary phases may cause severe tailing and peak distortion in the chromatograms, as well as a decrease in the effective throughput of intact proteins in preparative mode. Lysozyme is a hydrophobic and highly basic protein of moderate size, and is therefore well suitable as a probe for biocompatibility of separation media (Müller, W., J. Chromatogr., 1990, 510, 133–140). An experiment was consequently carried out on the SPE-copoly-EDMA zwitterionic monolithic sorbent prepared according to Example 6, under conditions similar to those practised in Example 12, to determine the recoveries of the proteins used as probes in Example 12 after the separation. The recovery for the relatively hydrophilic protein cytochrome C was found to be 96%, whereas the recovery for lysozyme reached above 85%, despite its pronounced hydrophobic character in combination with a totally aqueous eluting solution. The favorable hydrophilic properties of these zwitterionic stationary phases is also evident from the relative absence of tailing in the separation of the synthetic peptides, as disclosed in Examples 9 and 10. These peptides are small and highly hydrophobic, and are therefore known to "stick" strongly to hydrophobic moieties that may be exposed on chromatographic sorbents.

What is claimed is:

1. A sorbent suitable for use as a stationary phase in elution chromatography, the core of said sorbent consisting of an organic resin selected from the group consisting of polymers made from mono- or oligo-vinyl monomers and carbohydrates other than cellulose and wherein a plurality of non-aromatic zwitterionic groups are covalently bonded on the surface of said sorbent.

2. A sorbent according to claim 1, characterized in that the sorbent further comprises a porous carrier.

3. A sorbent according to claim 1, characterized in that the zwitterionic non-aromatic groups have been bound to the carrier by polymerizing monomers comprising non-aromatic zwitterionic groups on the surface of the carrier.

4. A sorbent according to claim 3, characterized in that the zwitterionic non-aromatic groups have been incorporated throughout the structure of the carrier sorbent by polymerizing monomers comprising non-aromatic zwitterionic groups together with suitable divinyl crosslinking monomers.

5. A sorbent according to claim 3, wherein the zwitterionic groups have been bound to the carrier by graft polymerizing monomers comprising non-aromatic zwitterionic groups on the surface of the carrier.

6. A sorbent according to claim 1, characterized in that the zwitterionic non-aromatic groups have been bound to the carrier by activation of the carrier with an alkylating functional group, which is subsequently reacted with an ω-dialkylamino-alkylsulfonic acid to form non-aromatic zwitterionic groups on the carrier.

7. A sorbent carrier according to claim 1, characterized in that the surface of the organic resin has been activated by incorporation of a reactive functional group that is capable of alkylating the amino group of an aminoalkylsulfonic acid in a reaction producing covalently bonded zwitterionic non-aromatic groups on the sorbent carrier.

8. The sorbent carrier of claim 7, wherein the reactive functional group is one of an epoxy and a halogenoalkyl.

9. A sorbent carrier according to claim 1, characterized in that the surface of the organic resin has been activated by incorporation of a reactive functional group that is capable of forming an ester or ether bond with a hydroxyl group residing on the alkyl chain interconnecting the quarternary ammonium group and the sulfonate group in a sulfobetaine zwitterion, thus covalently binding a non-aromatic zwitterionic group to the surface of the activated sorbent carrier in a lateral fashion.

10. The sorbent carrier of claim 9, wherein the reactive functional group is one of a hydroxyalkyl, a carboxylic acid, a carboxylic acid chloride, a carboxylic acid bromide, a carboxylic anhydride, a carboxylic ester, an alkyl oxonium, an epoxy, a chloroalkyl, a bromoalkyl, a diazoalkyl, and an activated amide.

11. A sorbent carrier according to claim 1, characterized in that the carrier is a polymeric monolith.

12. A sorbent carrier according to claim 1, characterized in that the zwitterionic groups are ω-sulfoalkyl-trialkylammonio (sulfobetaine) groups.

13. A sorbent, comprising:
   a core consisting of an organic resin selected from the group consisting of polymers made from mono- or oligo-vinyl monomers and carbohydrates other than cellulose;
   a sorbent surface; and
   a plurality of non-aromatic zwitterionic groups covalently bonded to said surface;

and wherein said sorbent has selective sorption properties so that said sorbent can be used as a stationary phase in chromatographic separations.

14. The sorbent according to claim 13, wherein said zwitterionic non-aromatic groups have been bound to the surface of the sorbent by graft polymerization of monomers comprising non-aromatic zwitterionic groups.

15. The sorbent according to claim 13, wherein said zwitterionic non-aromatic groups have been bound to the sorbent by activation with an alkylating functional group and then reacted with a ω-dialkylaminoalkylsulfonic acid to form non-aromatic zwitterionic groups on the sorbent.

16. The sorbent according to claim 13, wherein said sorbent is porous.

17. The sorbent according to claim 13, wherein said sorbent is porous and has pore diameters ranging from 0.01 to 10 μm.

18. A sorbent suitable for use as a stationary phase in elution chromatography, comprising:
   a core consisting of an organic resin selected from the group consisting of polymers made from mono- or oligo-vinyl monomers and carbohydrates other than cellulose;
   a sorbent surface; and
   a plurality of non-aromatic zwitterionic groups covalently bonded to the surface.

19. The sorbent according to claim 18, wherein said sorbent is a porous monolithic sorbent carrier.

20. The sorbent according to claim 18, wherein said zwitterionic non-aromatic groups have been bound to the surface of the sorbent by graft polymerization of monomers comprising non-aromatic zwitterionic groups.

* * * * *

(12) EX PARTE REEXAMINATION CERTIFICATE (6870th)

United States Patent
Irgum et al.

(10) Number: US 6,884,345 C1
(45) Certificate Issued: Jun. 9, 2009

(54) CHROMATOGRAPHY METHOD AND A COLUMN MATERIAL USEFUL IN SAID METHOD

(75) Inventors: Knut Irgum, Bullsmark (SE); Camilla Viklund, Umeå (SE)

(73) Assignee: Sequant AB, Umea (SE)

Reexamination Request:
No. 90/009,072, Mar. 7, 2008

Reexamination Certificate for:
Patent No.: 6,884,345
Issued: Apr. 26, 2005
Appl. No.: 09/831,162
Filed: May 7, 2001

(22) PCT Filed: Nov. 9, 1999

(86) PCT No.: PCT/SE99/02032

§ 371 (c)(1),
(2), (4) Date: May 7, 2001

(87) PCT Pub. No.: WO00/27496

PCT Pub. Date: May 18, 2000

(30) Foreign Application Priority Data
Nov. 9, 1998 (SE) .............................. 9803838

(51) Int. Cl.
| | | |
|---|---|---|
| B01J 43/00 | (2006.01) |
| B01J 20/32 | (2006.01) |
| B01J 39/26 | (2006.01) |
| B01J 20/30 | (2006.01) |
| B01D 15/26 | (2006.01) |
| B01D 15/08 | (2006.01) |
| B01D 15/36 | (2006.01) |
| G01N 30/00 | (2006.01) |
| G01N 30/52 | (2006.01) |

(52) U.S. Cl. .................. 210/198.2; 210/502.1; 210/635; 210/656; 502/402; 502/404

(58) Field of Classification Search ........................ None
See application file for complete search history.

(56) References Cited
U.S. PATENT DOCUMENTS
5,164,424 A 11/1992 Brueschke et al.

*Primary Examiner*—Dwayne C Jones

(57) ABSTRACT

A novel sorbent suitable for use as a stationary phase in a chromatography column, the core of which consists of an organic polymer of synthetic or natural origin. Further, the carrier exhibits a plurality of covalently bonded non-aromatic zwitterionic groups on its surface. Additionally, the invention also relates to a method for purifying a particular biological macromolecule, such as a protein or a nucleic acid, by zwitterionic ion exchange chromatography as well as an ion exchange column suitable for use in the zwitterionic ion exchange chromatography.

A)

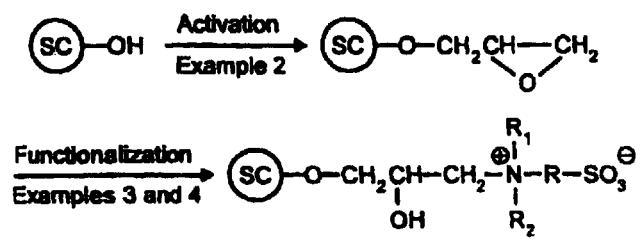

SC = Sorbent carrier

B)

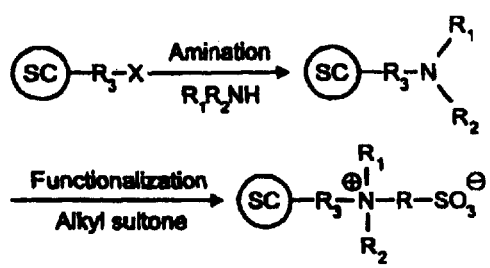

SC = Sorbent carrier

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 2–12, 14–16, 19 and 20 is confirmed.

Claim 17 is cancelled.

Claims 1, 13 and 18 are determined to be patentable as amended.

1. A sorbent suitable for use as a stationary phase in elution chromatography, the core of said sorbent consisting of an organic resin selected from the group consisting of polymers made from mono- or oligo-vinyl monomers and carbohydrates other than cellulose and wherein a plurality of non-aromatic zwitterionic groups are covalently bonded on the surface of said sorbent, *wherein said sorbent is porous and has pore diameters ranging from 0.01 to 10 μm*.

13. A sorbent, comprising:

a core consisting of an organic resin selected from the group consisting of polymers made from mono- or oligo-vinyl monomers and carbohydrates other than cellulose;

a sorbent surface; and a plurality of non-aromatic zwitterionic groups covalently bonded to said surface;

[and] wherein said sorbent has selective sorption properties so that said sorbent can be used as a stationary phase in chromatographic separations; *and*

*wherein said sorbent is porous and has pore diameters ranging from 0.01 to 10 μm*.

18. A sorbent suitable for use as a stationary phase in elution chromatography, comprising:

a core consisting of an organic resin selected from the group consisting of polymers made from mono- or oligo-vinyl monomers and carbohydrates other than cellulose;

a sorbent surface; and a plurality of non-aromatic zwitterionic groups covalently bonded to the surface, *wherein said sorbent is porous and has pore diameters ranging from 0.01 to 10 μm*.

* * * * *